United States Patent [19]

Natchev

[11] Patent Number: 4,535,762

[45] Date of Patent: Aug. 20, 1985

[54] MECHANICAL BIO-FEED-BACK AUTO-TRACTION BENCH

[76] Inventor: Emil J. Natchev, Upplandsgatan 50, S-113 28 Stockholm, Sweden

[21] Appl. No.: 521,357

[22] Filed: Aug. 8, 1983

[30] Foreign Application Priority Data

Apr. 6, 1983 [SE] Sweden ............................ 83018937

[51] Int. Cl.³ ............................................ A61F 5/00

[52] U.S. Cl. ........................................ 128/71; 5/67; 5/62

[58] Field of Search ................................ 128/70–75; 5/62–63, 66–69; 269/322–325

[56] References Cited

U.S. PATENT DOCUMENTS

| | | | |
|---|---|---|---|
| 1,270,737 | 6/1918 | Hyatt | 5/62 |
| 1,644,043 | 10/1927 | Tiedemann | 5/62 X |
| 3,806,109 | 4/1974 | Weber et al. | 269/323 |
| 4,002,165 | 1/1977 | Lind | 128/71 |
| 4,195,829 | 4/1980 | Reser | 269/325 |
| 4,425,673 | 1/1984 | Werner | 5/63 |

*Primary Examiner*—Richard J. Johnson
*Attorney, Agent, or Firm*—Larson and Taylor

[57] ABSTRACT

A mechanical bio-feed-back auto-traction bench, preferably for treatment of skeleton and soft body tissue lesions and comprising a support frame which carries a support bed (3) for a patient and in which the support bed is divided in the longitudinal direction of the bench into a head component (18) and a foot component (19) which are both rotatable upwards and downwards (α, β) independently of each other around a connection bar (15) provided between the two parts. The support frame comprises a supporting bottom frame (1) in which the bench frame (2) is rotatably mounted (δ). The bench frame (2) in turn carries the two component support bed (18, 19), and between the bench frame and the head component (18) and the foot component (19) respectively means are provided for rotating each component up or down (α, β) and possibly for side rotating the head component (18) in either direction. For rotating the head and foot components (18, 19) in the longitudinal direction and for side rotating the head component and possible for raising and lowering the support bed (3) and for tilting the bench frame (2) together with the support bed (3) into an optional angle (δ) in relation to the bottom frame (1) there is a system of power actuated means which preferably are mounted in the base between the bottom frame (1), the bench frame (2) and the support bed (3).

14 Claims, 8 Drawing Figures

MECHANICAL BIO-FEED-BACK AUTO-TRACTION BENCH

The present invention generally relates to auto traction benches for treatment of spinal conditions of a human being and of the type which comprises a support which carries a bench on which the patient is resting during the treatment and to which the patient is clamped with some part of the body whereas a traction means is applied to another part of the body so that a stretching can be provided between the soft body portions and the skeleton portions between the attachment means and the traction means, especially a stretching of the spine. Two main types of such traction benches are previously known. One type is formed as a bench on which the patient is lying in a substantially horizontal plane on his back or on his face during the treatment, and the second type is formed as a stretching means in which the patient completely or partly is hanging during the treatment.

The first mentioned type of traction benches may in a highly development bench type be formed as shown in the U.S. Pat. No. 4,002,165 in the name of Gertrud A. M. Lind, in which the bench is parted in the longitudinal direction into two bench parts which are independent of each other and which may separately be rotated over a slight angle in relation to a common cross mounting bar, and in which the apparatus preferably is formed so that the patient himself or herself can provide the stretching in that the hip portion of the patient is strapped against the foot part of the bench by means of a waist belt whereas the patient pulls himself or herself to a stretched condition in a direction opposite from the foot part of the bench in that the patient with the hand grip attachement bars at the head part of the bench and by means of his or her own arm force provides the stretching. For providing the best position the patient may lie on his or her face or back and the head part as well as the foot part of the bench can be rotated to an upwards or downwards sloping position in which the patient feels to have the best position with least pain.

In many cases this previously known auto-traction gives good results, but function is limited in some respect. The bench is mainly only suited for treatment of disc hernia in the lumbar or low back region, on the contrary the bench is not suited or less suited for treament of soft body portions and skeleton portions of the chest back region (toracal) or the neck back region (cervical). Depending on skeleton lesions the patient may in many cases have difficulties in reaching and gripping the traction bars mounted at the head part of the bench. Depending on lack of muscle strength other patients may have difficulties in providing, by his or her own arm force, the necessary stretch force for the treatment. Patients having pains may also in the horizontal position have difficulties in finding a position in which the pain is a minimum.

The second main type of traction benches or traction instruments, in which the patient completely or partly is hanging strapped in a head halter, a chest belt or a similar attachment means generally gives a more complete treatment of the entire spine, but this type of traction bench, in turn, does not make it possible for the patient to look for the best position or a position in which the patient has minimum of pain, it is not possible to raise or lower the foot part and the head part of the bench respectively independently of each other, and the patient has no possibility of continuously or fluctuatingly change the stretch force according to his or her own choice like the patient may do in the first mentioned type of traction bench by providing the stretching force by means of the patient's arm force.

Some traction instruments of the said second main type are designed so that the patient is sitting, standing or hanging freely while, other instruments are formed with a solid bench on which the patient is resting while the bench is titled to a large or small angle, whereby the traction force is varied correspondingly. In both case the above mentioned disadvantages and short-comings are present.

The present invention intends to overcome the disadvantages and short-comings of the previously known traction benches and to provide a comprehensively operating mechanical auto traction bench for treatment of skeleton and soft body part lesions, which combines the advantages of the above mentioned main types of traction benches and which does not have disadvantages and short coming of any of said previously known traction benches.

In the attempt to combine the two above mentioned main types of traction benches some technical problems arise. To easily get on to the bench when in a horizontal position it is important that the bench is not higher than a normal treatment bench, for instance a fixed horizontal traction bench. At the same time it is necessary that the bench in the tilted-up position does not reach a too high level with one end and does not hit the floor with the opposite end. Further the point of rotation must not be located especially close to one end of the bench, for instance the foot end of the bench, since in such case the bench is unstable and this may hazard the treatment in that the patient gets a feeling of unsafety and is not relaxed. Further it is not allowed that the bench upon tilting reaches a point of balance which is displaced so that the bench as an entire unit is strongly unevenly loaded. Also it cannot be allowed that the support wheels or the support legs of the bench, in order to maintain the stability, are located very far out of the horizontal bench area since they may in such case prevent a free movement of the doctor or the treating persons which have to move around the bench.

In the above mentioned type of auto traction bench in which the foot end and the head are freely rotatable some distance up and down independently of each other there are special problems in that the means for providing such rotation must give a stable attachment point towards the support frame of the traction bench and in that said means preferably are located between the rest support of the patient and the support frame of the bench and thereby prevent a free mounting of the further means which are necessary for tilting of the bench.

Therefore the invention relates to an auto-traction bench comprising a support frame which carries a support bed for the patient, in which the support frame is divided into a head also referred to as an upper body section, and a foot, also referred to as a lower body portion, in the longitudinal direction of the bench, and in which both the upper body section and the lower body section are provided for being rotated over a predetermined angle upwards and/or downwards from a mounting means located between the upper body section and the lower body section, and in which means for providing a rotation upwards and/or downwards are mounted between the support frame and the upper body section and the lower body section respectively of the bench. The traction bench according to the invention is intended for use in treatment of many types of lesions in the soft body portions and the skeleton of the patient whether the lesions are located in the legs, or in the loin region, the hip region, the chest region or the neck region, and in which the bench can be used even for patients having such weak muscle forces or having such painful lesions that the patient cannot himself provide the traction force with the arms. The invention also includes a method of using the auto-traction bench of the present invention.

In a special embodiment of the invention at least the upper body section or the lower body section of the bench, preferably the upper body section, is further adapted for being rotated in one direction or the other around a longitudinally extending central shaft, whereby special treatment effects can be obtained and whereby optimum possibilities are gained for finding a treatment position in which the patient has a minimum of pain. In such position a muscle relaxation is obtained rather than the usual pain spasm which is the normal reaction in the soft body portions at conflict between hard tissue and pain sensitive tissues of the body. Further the traction bench is also intended for being used as an ordinary mobile bench and for special medical treatment in which the upper part of the body of the patient ought to be positioned sloping downwards, for instance in case of a postural drainage, etc.

According to the invention a support surface comprising a support frame and support bed of the traction bench are provided for being tilted as an integral unit independently of the different rotated positions which are adjusted at the upper body sections or lower body sections of the support frame, and for this purpose the traction bench is formed as a supporting bottom frame, also referred to as a lower supporting frame or a lower frame, in which a bench frame together with the support frame and support bed for the patient is rotatably mounted and provided for being adjusted to any optional position tilted up from the bottom frame and to safely rest in the bottom frame when in its down position, and in which the means for providing the tilting movements of the upper body sections and/or the lower body sections of the support frame are mounted between the rotatable bench frame and the bottom frame.

Preferably the axis of rotation between the bottom frame and the bench frame is provided on a relatively high level, for instance a slight distance below the support bed, and in order to enable a tilting up of the bench frame over a substantial angle, the axis of rotation between the bottom frame and the bench frame is provided between the common axis of rotation for the upper body section and the lower body section on one hand and the foot end of the support bed on the other hand and in such position that the support frame, with the bench frame fully tilted up is located close to the floor level. At the same time it is foreseen that the axis of rotation of the bench frame is positioned so close to the common axis of rotation for the upper body section and lower body section of the support frames that the centerline of gravity for the support bed together with the patient in the fully titled up position is located a substantial distance inside the area defined by the support legs or the support wheels, and that the support legs and the support wheels are positioned inside the floor area occupied by the bottom frame, the bench frame or the support frame.

Further features and advantages of the invention will be evident from the following detailed description in which reference will be made to the accompanying drawings. It is, however, to be understood that the described embodiments of the invention only are illustrating examples and that many different modifications may be presented within the scope of the appended claims.

In the drawings FIG. 1 is a diagrammatically illustrated perspective view of a traction bench according to the invention.

Figure 5:
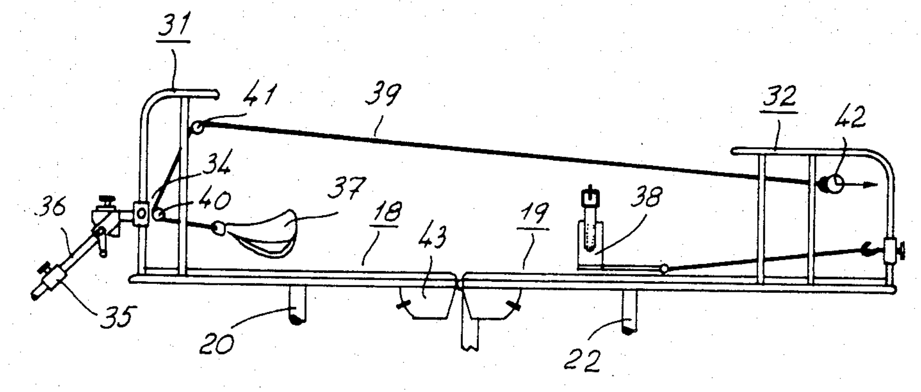
Figure 6:
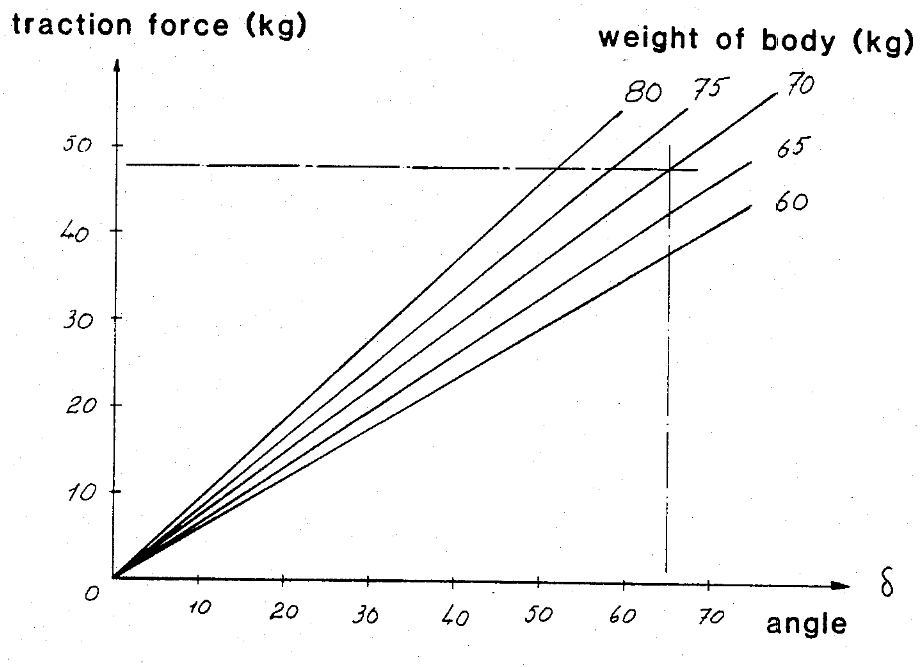

FIG. 5 diagrammatically shows a couple of different types of connection means for the patient, and FIG. 6 shows a diagram over the traction force which is obtained when the traction bench is tilted up in different angles.

Figure 7:
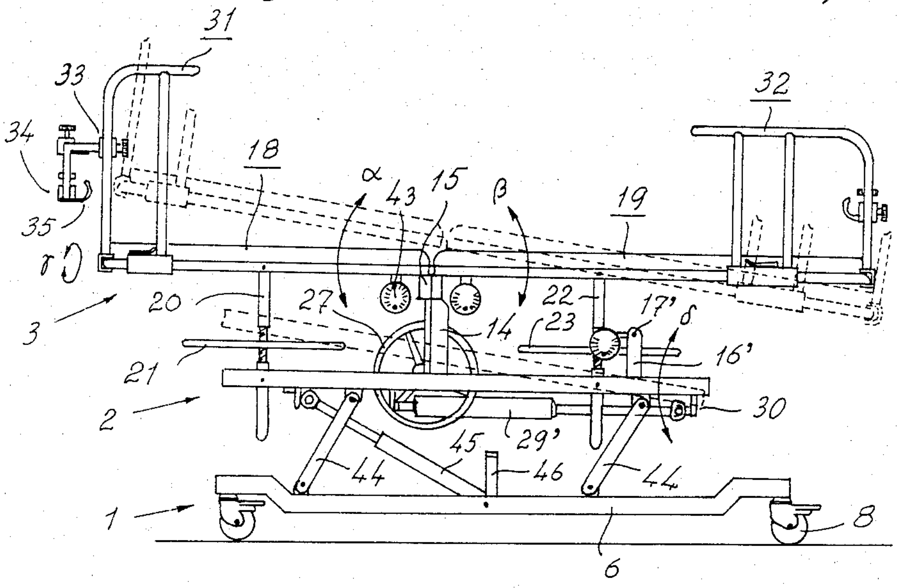
Figure 8:
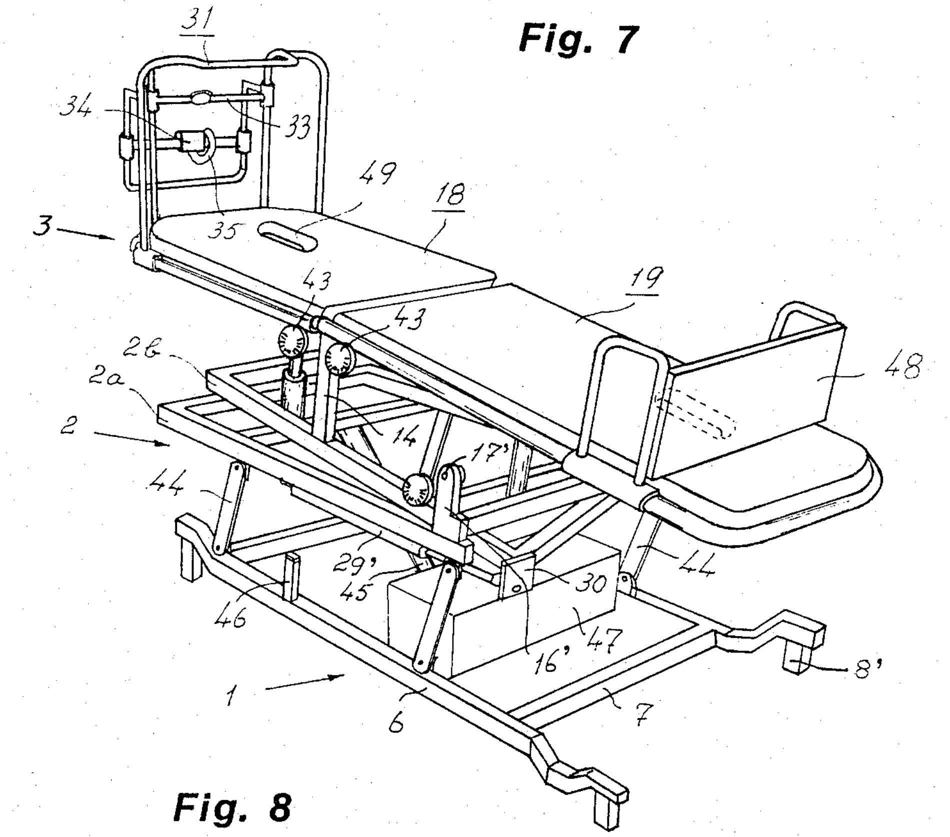

FIG. 7 is a partial side view of an alternative embodiment of a traction bench according to the invention, and FIG. 8 is a perspective view of a further modified emobiment of a traction bench according to the invention in a slightly tilted up position.

Figure 1:
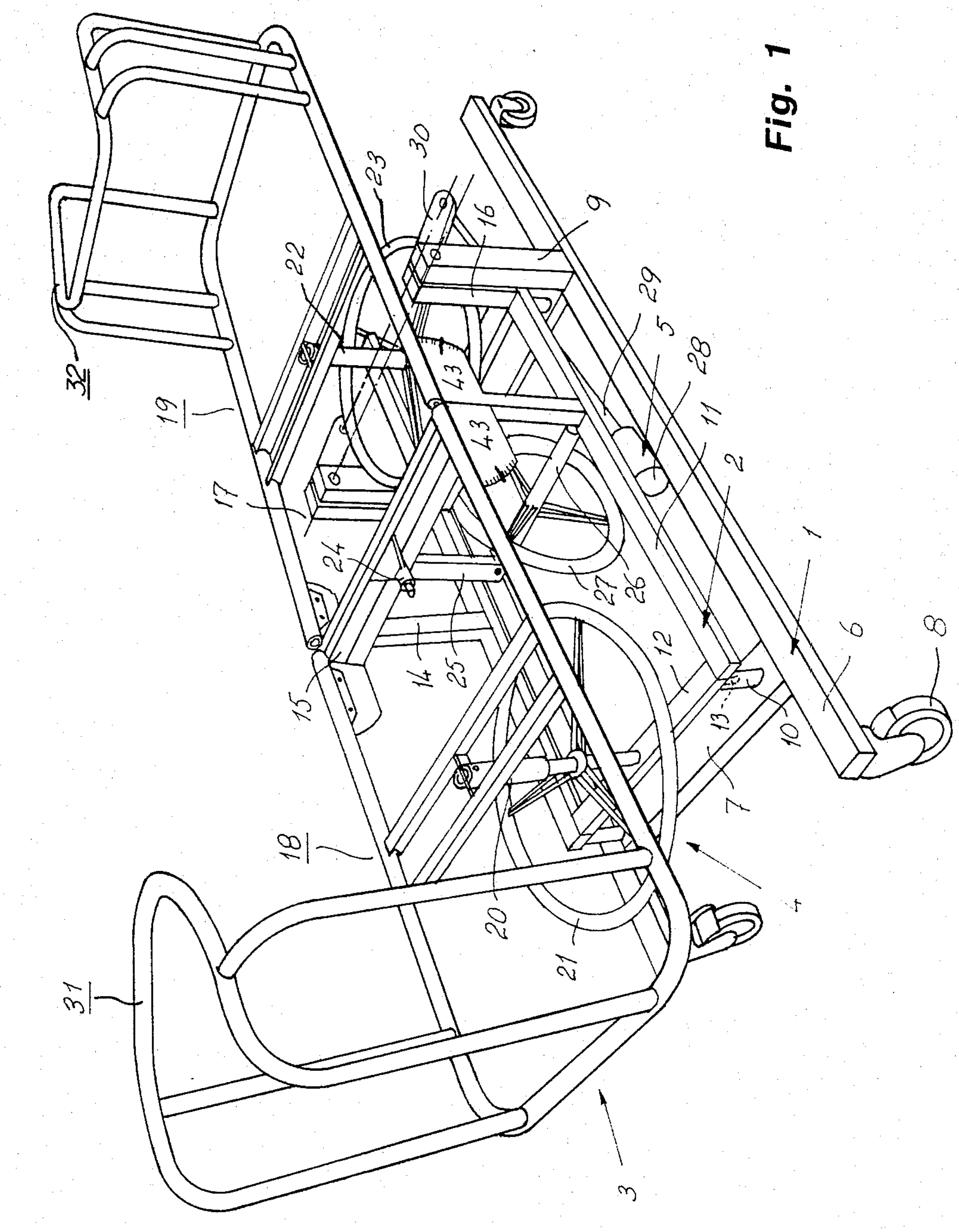

For the sake of clarity the traction bench illustrated in FIG. 1 is shown without the support bed on which the patient normally lies during the treatment. Generally the traction bench comprises a supporting bottom frame 1, or lower frame, a bench frame 2, a support frame 3, means 4 for rotating the different section of the support frame and means 5 for tilting the bench frame 2 in relation to the bottom frame 1. Within the scope of the invention the traction bench can be formed with means (not illustrated in FIG. 1) for raising and lowering the bench frame together with the support frame independently of the rotation and tilting movements of the support frame.

The bottom frame 1 is formed as a solid rectangular frame preferably made of metal bars and comprising longitudinal bars 6 and cross bars 7. At the end of the longitudinal bars the bottom frame is carried by wheels 8. The bottom frame is designed with such length and width that the entire bottom frame together with the support wheels are located inside the floor area below the support bed. Thereby it is possible for a person to move freely around the traction bench. At a place located some distance in the direction toward the foot end of the traction bench the bottom frame is formed with upright bars 9 in which the bench frame 2 is rotatably mounted. On one of the cross bars 7 the bottom frame is formed with a carrier 10 for supporting and securing the bench frame in the horizontal plane.

Like the bottom frame the bench frame 2 is formed as a rectangular frame having longitudinally extending bars 11 and cross bars 12 and, at least the end where the bottom frame is formed with the carriers 10, the bench frame is formed with corresponding pins 13 for engaging in the carriers 10. At a place along the longitudinal bars 11 the bench frame carries upright bar 14, the upper ends of which are interconnected by a cross bar 15 providing a fixed connection point for the support frame. At a place corresponding to the upright 9 of the bottom frame, the bench frame is formed with an upright 16. The uprights 9 and 16 extend to a level just below the support bed, and the upper ends of the said uprights are rotatably interconnected by a cross shaft 17. Thereby the bench frame may be tilted up still in contact with the bottom frame.

In the conventional way the support frame is divided into an upper body section or part 18 and a lower body section or part 19 which are both rotatably connected to the cross bar 15 located generally at a central portion of the support frame. For tilting the upper body section 18 up or down there is a mechanical, electrical or hydraulic raising or lowering apparatus, for instance a screw-nut apparatus 20, which is mounted between the bench frame and the support frame and which can be actuated by an actuation wheel 21. Correspondingly a raising and lowering apparatus like a screw-nut apparatus having an actuation wheel 23 is connected between the bench frame and the support frame at the lower body section of the support bed.

In the illustrated embodiment the upper body section 18 is rotatable in the transverse direction, and for this purpose the upper body section is rotatably mounted in a longitudinal shaft 24. From a point of the upper body section located adjacent the shaft 24 at the cross bar 15 an arm 25 extends downwards. The lower free end of said arm is connected to a third raising and lowering apparatus, for instance a screw nut apparatus 26 having an actuating wheel 27. The opposite end of the screw nut apparatus 26 is connected to a part of the bench frame 2. By actuation of the wheels 21, 23 the upper body section and the lower body section of the support frame can be rotated upwards and/or downwards some distance for instance an angle $\alpha$ and $\beta$ respectively of 10°, and in addition thereto by wheel 27 the upper body section 18 may independently of the tilting movement be rotated in one direction or the other about the longitudinal central shaft 24, for instance an angle $\gamma$ of between 10° and 20°.

Figure 4:
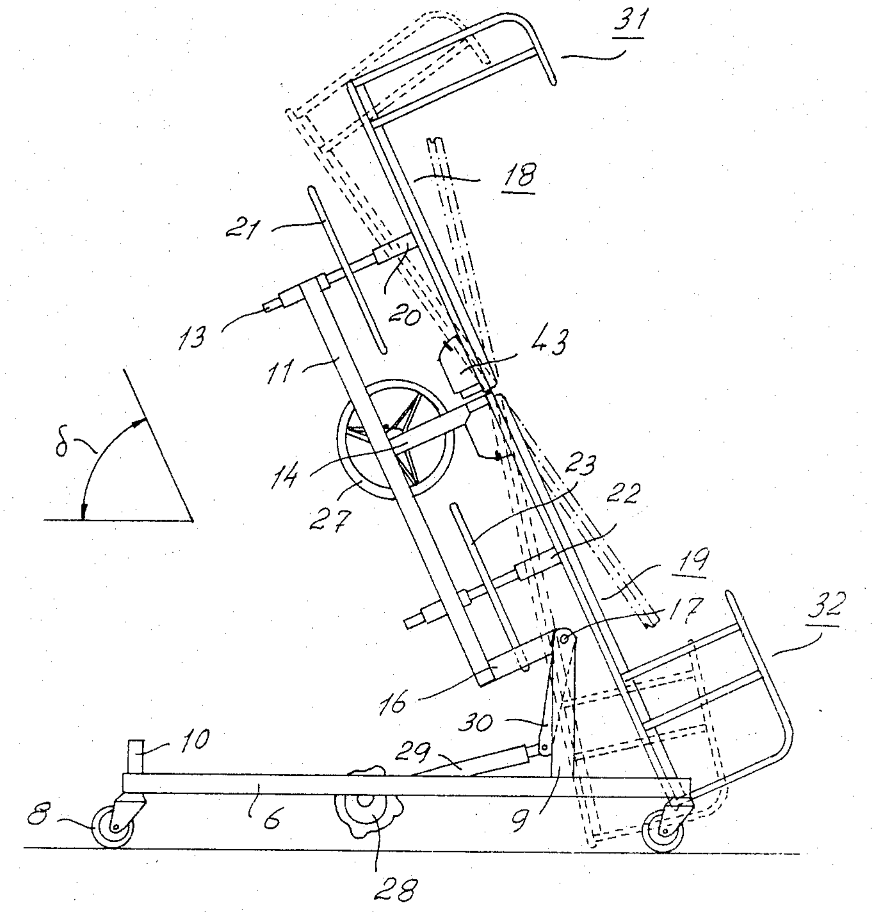
FIG. 4 shows the bench according to FIGS. 2 and 3 in its fully tilted up position.

For providing a tilting upwards of the bench frame 2 from the bottom frame 1 there is an actuation means for instance an electrical or electro hydraulic motor 28 which over an axially operating ball-screw or a hydraulic cylinder 29 is adapted to actuate a projecting arm 30 of the bench frame. In the illustrated case the arm 30 is connected to the upright bar 16, and when actuating the motor 28 in one direction the bench frame is tilted upwards (with the head part), and when actuating the motor in the opposite direction the bench frame is tilted down. By calculating both the distance between the end of the foot component 19 and the rotation shaft 17 for the bench frame and the vertical distance from the floor plane to the rotation shaft 17 a suitable maximum tilting angle $\delta$ can be predetermined. As best illustrated in FIG. 4 the apparatus has been given a tilting angle $\delta$ of about 65° in the above described illustrated case.

The traction bench can be used both in its tilted down, horizontal position and in a position tilted up to any angle $\delta$ as far as to the maximum tilting angle. Depending on what disease is to be treated, a suitable position for the support bed is chosen. The upper body section and the lower body section of the support bed are tilted up or down to an angle $\alpha$ and $\beta$ respectively independently of each other by actuation of the wheels 21 and 23, and in addition thereto the upper body section can be rotated in one direction or the other over an angle $\gamma$ by the actuation of the wheel 27. It should be noted that such actuation also is possible even if the bench frame 2 is tilted up into any angle $\gamma$ in relation to the bottom frame. Thereby it is possible to search the best position for the patient, especially a position in which possible pains have a minimum, and the treatment can be carried out in the most effective and at the same time the least painful way.

In a preferred embodiment of the invention all raising, rotation and tilting happen by actuation means such as hydraulic cylinders, which are connected to a common electro-hydraulic motor and which can be handled over a control panel both by the doctor and the nurse and by the patient for adjusting the exactly wanted position, especially a position in which the patient feels a minimum of pain. The auto-traction bench also can be formed so as to be raised and lowered as required by means of a hydraulic cylinder connected to the common hydraulic source of power.

Figure 2:
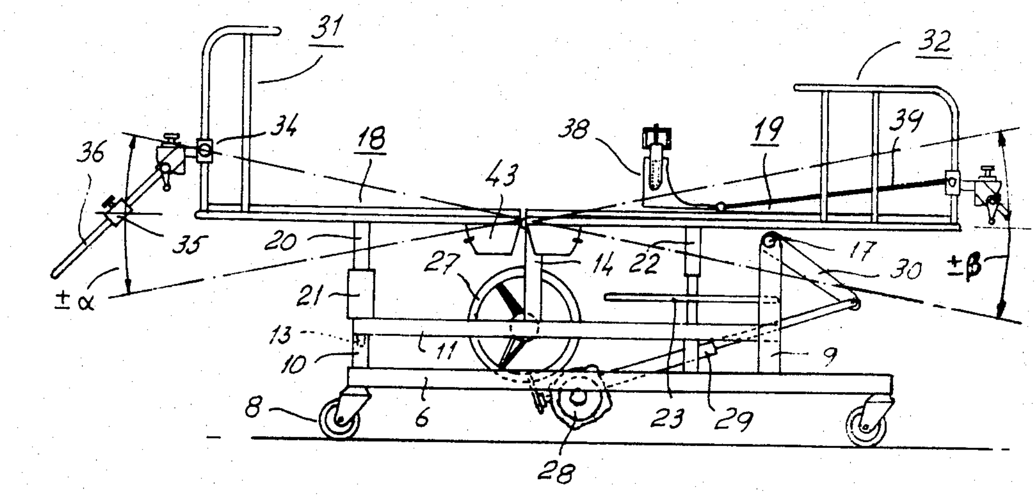
FIG. 2 is a side view of the bench according to FIG. 1 in its fully tilted down position.
Figure 3:
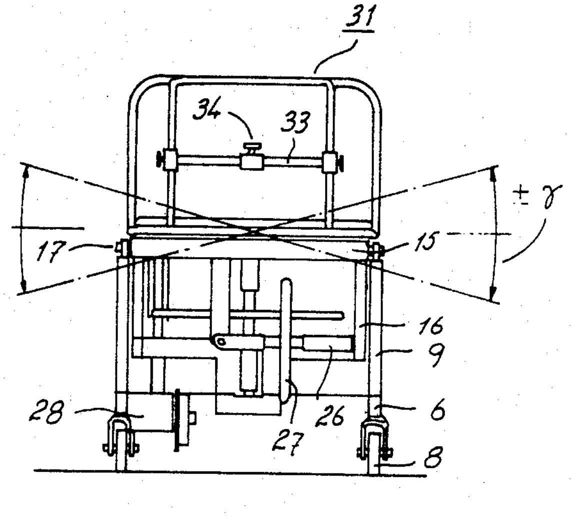
FIG. 3 is an end view from the left end, viz. the head end of the bench in FIG. 2.

During the treatment the patient has to be strapped into the support bed in any way, and therefore the support frame in previously known way is provided with an upwards projecting head frame 31 and a corresponding upwards projecting foot frame 32. Preferably both frames are detachable so that alternative means may be attached to the bench, or the bench may be used for transporting patients. In order to make it possible to strap the patient in any optional point of the head frame and the foot frame a mounting means is used which is best shown in FIGS. 2 and 3. The said mounting means comprises a cross bar 33 which is vertically adjustable on a pair of bars in the head frame 31 and the foot frame 32. The cross bar 33 displacebly carries a horizontally movable slide 34 which in turn carries an attachment hook 35 provided on a projecting bar 36 which is adjustable to an optional angle. A corresponding mounting means is provided at the foot part of the support bed. For strapping the patient in the mounting means may be used, for instance a head halter, a waist belt, a chest belt, a hip belt or any other previously known means which is strapped to the upper body section or the lower body section of the support frame by means of a lengthwise adjustable wire.

In such traction operation, named auto-traction, in which the very patient causes the traction by his or her own power the patient is strapped to the lower body section of the support frame. In case of traction without the assistance of force by the patient, whereby the bench frame is tilted up by the actuation of the motor the patient is strapped to the upper body section for instance by means of a head halter, a chest belt or a waist belt. It should be noted that the patient himself or herself may control the traction in stretching or releasing direction even when the bench frame is tilted in that the patient with arm power counteracts the traction force obtained by the gravity power.

In FIG. 5 is shown an example of a traction procedure in which the patient is fixed strapped to the lower body section part by means of a hip belt 38 and is movably strapped to the upper body section by means of a head halter 37. The apparatus shown in FIG. 5 is used for providing a traction in the horizontal position of a patient having weak arm power, and in this case the patient may provide the traction power by means of his or her leg power. This is possible in that the head halter 37 is connected to a wire 39 extending over two pulleys 40 and 41 connected to the head frame 31 and which at the end is connected to a longitudinally displacable slide 42 against which the patient may put his feet thereby pushing the slide towards the foot frame, whereby a traction is provided from the head halter 37 to the hip belt 38.

As mentioned above the traction may be provided either as an auto-traction in that the patient himself provides a traction force by his arms or legs in a direction from the strapping point, or as a gravity actuated traction in that the bench frame together with a support frame is tilted. In the latter case the patient possibly also may periodically increase or reduce the traction force by actuating with his own arm or leg power the projecting head frame or foot frame.

By tilting the bench frame together with the support bed to different angles different gravity traction forces are obtained, and in FIG. 6 is shown a diagram over the gravity traction force at different tilting angles δ of the support bed. With full lines in the diagram are shown the gravity traction forces for patients having the body weights of between 60 and 80 kg. In this diagram the friction coefficient between the patient and the support bed was assumed to be 0.1 and the traction was intended for treatment of parts of the spine. It is obvious to the expert that the friction coefficient may vary and depends on different designs of the support belt, and that traction treatments may be made of other parts of the body than the spine. It is obvious that the traction force from the value zero for a 70 kg patient on a horizontal support bed increases to about 48 kg for a tilting angle δ corresponding to 65°. In the embodiment shown in FIGS. 2–4 it is presupposed that 65 degrees is the maximum tilting angle. Of course the maximum tilting angle may be made higher or lower than 65°.

As previously mentioned the upper body section 18 and the lower body section 19 of the support frame can be rotated up or down from the intermediate cross bar 15 independently of each other at any tilting angle of the bench frame together with the support frame, and at the same time the upper body section may be rotated to one side or the other around the longitudinal central shaft 24, and that it is consequently possible to search and find, in an optimum way, the best position for the patient. Further the connection point at the head frame 31 or the foot frame 32 for the head halter, the chest belt, the waist belt, the hip belt etc. can be adjusted both in the vertical direction and in the horizontal direction, whereby both the actual best traction direction and traction force can be obtained. For making of the rotation angle, the tilting angle and the side rotation angle there are suitable marking devices such as marking plates 43.

As evident the described apparatus may be adjusted according to the following five operations:

- rotation upwards or downwards to an angle α of the upper body section 18
- rotation upwards or downwards to an angle β of the lower body section 19
- side rotation in the right or left direction to an angle γ of the upper body section 18
- tilting upwards to an angle δ of the entire support frame 3
- raising or lowering the entire support frame 3 (this aspect is illustrated in FIGS. 7, 8).

When treating patients having pains depending on tissue reaction caused by mechanical conflict between hare tissue and pain sensitive soft tissues of the body, the traction bench at first is adjusted to a position in which the patient has a minimum of pain and the patient is maintained in this position for some time, for instance 10–30 minutes so that the pain is reduced as far as possible and the muscles of the patient become relaxed. This is a precaution for a good result of the treatment. After the lapse of said period one or more tractions are made, either by the patient or with the assitance of the nursing people. The relaxation and the tractions may be made both with the bench in the horizontal position or the bench tilted to any wanted angle. The treatment including the relaxation and the tractions is preferably repeated several times.

FIGS. 7 and 8 illustrate two further embodiments of a traction bench according to the invention, in which the bench frame together with the support frame can be raised and lowered. In order that the patient should be able to conveniently get on to the support bed, the bed ought to be rather low. Such low bed, however, is inconvenient for the doctor or the nursing people, and also a low support bed cannot be tilted to the intended maximum angle since the lower body section of the support frame thereby gets in contact with the floor. Therefore the bench frame 2 together with the support frame, the rotation means and the tilting means can be raised and lowered respectively from the bottom frame 1. This is achieved by connecting the bench frame 2 to the bottom frame 1 over four pivot arms 44 providing a parallelogram. The bench frame is raised by means of a hydraulic cylinder 45 which at one end is connected to the bottom frame 1 and with the opposite end is connected to the bench frame 2. For supporting the bench frame in its down position the bottom frame is provided with support posts 46.

In this embodiment of the invention the bench frame 2 is divided into a support bench frame *2a* and a tilting bench frame *2b* provided inside the support bench frame 2. The support frame is rotatably connected to the support bench *2a* at the end thereof facing the lower body section of the support frame and over a cross shaft 17'. A hydraulic cylinder 29' for tilting of the tilting bench frame *2b* is with one end connected to the support bench frame *2a* and with the opposite end to a bar 16' projecting from the tilting frame *2b*. For maximum of safety the hydraulic cylinder 29' is of the contracting type in which the cylinder is expanded in the non-tilted condition and is contracted when tilting the support bed.

The traction bench in FIG. 7 is of the semi-hydraulic type, in which the raising and the lowering of the bench frame together with the support frame and the tilting is made hydraulically whereas the rotation of the upper body section and the lower body section and the side rotation of the upper body section is made by screw and wheel means 20–21, 22–23 and 26–27 respectively.

The traction bench shown in FIG. 8 is of the fully hydraulical type in which both the raising and the lowering of the support bed, the tilting of the support bed, the rotation of the upper body section and the lower body section, and the side rotation of the upper body section is made by means of hydraulic cylinders. Preferably there is a hydraulic central unit 47 mounted in the bottom frame 1 which co-ordinates the different hydraulic operations and which connected to a control panel from which all movements can be operated.

Preferably the head frame 31 and the foot frame 32 are detachably mounted on the support frame so that they can be removed in case the bench is used as a movable bench, or so that they can be substituted by other means. In a preferred embodiment of the invention the foot frame is substituted by a foot plate 48 on which the patient may stand when the support frame is tilted to the maximum angle which may be as high as 80°.

In order to give the traction bench a good stability during treatment of patients it is preferably formed both with support wheels for movement of the bench and support feet for having the bench steadily standing during the treatment. The support bed may be formed with two breathing holes, 49, one at the upper body section and one at the lower body section.

In a highly sophisticated embodiment of the invention the means for rotating the upper body section and the lower body section of the support and the means for tilting the frame are connected to a computer for calculating and registering the different adjusted angles according to the type of disease. The computer may provide the necessary adjustment according to calculated datas. Further the traction bench may be connected to an X-ray unit which on a TV-screen shows the position of the bones of the patient and the angles to which the different parts of the bench are adjusted.

I claim:

1. A traction bench for the traction treatment of spinal conditions of human beings, comprising:

a lower frame;

a bench frame pivotally connected to the lower frame for rotation about a transverse axis adjacent an end of the bench frame;

a support frame carried by the bench frame and divided into an upper body section and a lower body section which meet at a central portion of the support frame, each of said upper body section and lower body section being connected to the bench frame in the vicinity of said central portion by a pivot axis providing pivotal movement of each section independently of the other relative to the bench frame, a support bed carried by the support frame for receiving a patient to be treated, said support bed having a head part on the upper body section of the support frame and a foot part on the lower body section of the support frame;

means for rotating the upper body section about its said pivot axis to raise or lower that portion of the patient's body supported thereby;

means for rotating the lower body section about its said pivot axis to raise or lower that portion of the patient's body support thereby;

whereby the pivotal adjustments of the upper body section and the lower body section allow either of said sections to be inclined upwardly from the central portion to the opposite end thereof, with the other of said sections inclined downwardly from the central portion to the opposite end thereof to arrange the support frame and support bed inclined either upwardly or downwardly from the said opposite end of the upper body section to the said opposite end of the lower body section;

means for mounting at least one of said upper body or lower body sections for rotation about a longitudinal axis to impart torsional movement to the body of a patient thereon and means for rotating said at least one section about said longitudinal axis;

means for rotating the bench frame about said transverse axis for elavating one end of the bench frame to elevate the corresponding end of the support frame and support bed for traction treatment of a patient thereon by a gravational force;

said means for raising the bench frame, said means for pivoting at least one of the upper body or lower body sections and said means for rotating one of said sections about a longitudinal axis all being operable independently of each other, to permit the body of a patient carried by said bench to adjust to different angular and torsional positions during different relevant positions of the upper body and lower body sections relative to each other and during different elevations of the bench frame relative to the lower frame.

2. A traction bench according to claim 1, wherein said transverse axis between the lower frame and the bench frame is located at a height above the lower frame close to the level of the support bed when the support bed is horizontal.

3. A traction bench according to claim 1, including an upright bar on each longitudinal side of the lower frame, which bars act as holders for the bench frame, and wherein the bench frame is mounted adjacent the lower frame and is also provided with upright bars on each longitudinal side, whereby the two sets of uprights bars at their upper ends are connected by a shaft to from said transverse axis.

4. A traction bench according to claim 1, wherein the entire support frame is mounted to be raised and lowered independently of the adjustments made to the upper body section and lower body section and independently of the tilting of the bench frame.

5. A traction bench according to claim 1, including hydraulic power actuated means actuatable independently of each other from a common control panel for controlling rotating and tilting movements of the support frame and bench frame.

6. A traction bench according to claim 5, wherein the entire support frame is mounted to be raised and lowered independently of the adjustments made to the upper body section and lower body section and independently of the tilting of the bench frame, and including power actuated means for raising and lowering the support frame.

7. A traction bench according to claim 1, wherein the means for pivotally rotating the upper body section and the means for pivotally rotating the lower body section upwards and downwards are screw-nut means having actuating wheels mounted between a crossbar of the bench frame and the support frame for providing rotation of said sections even in the tilted up position of the bench frame.

8. A traction bench according to claim 2, including power means for tilting the bench frame together with the support frame, said power means being fixed relative to the lower frame and including an extendable and retractable means connected to a part of the bench frame which is spaced from the transverse shaft.

9. A traction bench according to claim 1, wherein the upright bars which interconnect the lower frame with the bench frame are located at a distance from the said opposite end of the lower body section such that the bench frame together with the support frame can be tilted to an angle of about 66°, whereby the lower body section is located close to the floor level.

10. A traction bench according to claim 4, including means for mounting the bench frame on the lower frame including at least two pivot arms on each longitudinal side, whereby the bench frame can be moved between the lower position in which the bench frame rests on the lower frame and an upward-forward rotated position in which the bench frame is located spaced above the lower frame.

11. A traction bench according to claim 10, wherein the bench frame comprises a support bench frame which can be moved between a lower position and a raised position parallel to the lower frame and a tilting bench frame which is rotatably mounted in relation to the support bench frame and in which the titing bench frame is movable independently of the support bench frame.

12. A traction bench according to claim 11, wherein the entire support frame is mounted to be raised and lowered independently of the adjustments made of the upper body section and lower body section and independently of the tilting of the bench frame relative to the lower frame, and including a power actuated means to effect said tilting means and wherein said power actuated means is mounted so that it can only be actuated when the support bench frame together with the tilting bench frame and the support frame are in their extreme raised position relative to the lower frame.

13. A method of treating spinal conditions of human beings by traction, comprising the steps of:

arranging the patient on a generally horizontal support surface, adjusting the position of the patient to eliminate or reduce discomfort by any one or more of the following adjustments, as required, including (1) adjusting the support surface to adjust the upper part of the patient vertically, (2) adjusting the support surface to adjust the lower part of the patient's body vertically, and/or (3) turning a portion of the support surface to turn either the upper or lower part of the patient's body about a longitudinal axis, while maintaining the other part of the patient's body against rotation, and combining said adjustments to eliminate or reduce discomfort, raising one end of the patient relative to the other end while securing the upper most part of the patient's body relative to the said surface until the inclination of the patient is sufficient to allow gravity to pull the part of the patient below the place where it is secured to effect traction by gravitational force on the patient's body, and while the patient is in the inclined position subjected to traction by a gravitational force, repeating the steps of eliminating or reducing discomfort by repeating the said adjusting steps, again combining them to eliminate or reduce discomfort.

14. The method of claim 13 wherein the adjustment steps are carried out by the patient on the support surface.

* * * * *